(12) United States Patent
Pinkerton

(10) Patent No.: US 9,975,002 B2
(45) Date of Patent: May 22, 2018

(54) SYNCHRONIZED EXERCISING AND SINGING

(71) Applicant: Ross Philip Pinkerton, Toronto (CA)

(72) Inventor: Ross Philip Pinkerton, Toronto (CA)

( * ) Notice: Subject to any disclaimer, the term of this patent is extended or adjusted under 35 U.S.C. 154(b) by 340 days.

(21) Appl. No.: 14/707,437

(22) Filed: May 8, 2015

(65) Prior Publication Data

US 2016/0325145 A1    Nov. 10, 2016

(51) Int. Cl.
*G10H 1/36* (2006.01)
*A63B 24/00* (2006.01)
(Continued)

(52) U.S. Cl.
CPC ...... *A63B 24/0075* (2013.01); *A63B 24/0087* (2013.01); *A63B 71/0622* (2013.01);
(Continued)

(58) Field of Classification Search
CPC ............ A63B 24/0075; A63B 24/0087; A63B 71/0622; A63B 22/0605;
(Continued)

(56) References Cited

U.S. PATENT DOCUMENTS 5,319,452 A * 6/1994 Funahashi ................ G10H 1/36 348/E5.099
5,588,842 A * 12/1996 Nishimura ............. G09B 5/065 348/478

(Continued)

FOREIGN PATENT DOCUMENTS

JP 2002140080 5/2002
KR 20110115995 10/2011

OTHER PUBLICATIONS

"The Peloton Bike", retrieved from https://www.pelotoncycle.com/bike accessed on May 27, 2014.
(Continued)

*Primary Examiner* — Jeffrey Donels

(57) ABSTRACT

A computer-implemented method and system facilitating a karaoke performance while exercising during an individual exercise session or group exercise class are disclosed. An indication of a song to be performed during the session or exercise class is received. At least one computer-readable karaoke file corresponding to the song is retrieved. The at least one computer-readable karaoke file may comprise common data elements, at least two independent karaoke data streams and exercise-related data elements. From a first class participant a selection of a first data stream of the at least two independent karaoke data streams is received. From a second class participant a selection of a second data stream of the at least two independent karaoke data streams is received. The presentation of the common data elements and the exercise-related data elements on a display common to the first and the second class participants is directed. The presentation of the first karaoke data stream on a display unique to the first class participant is directed. The presentation of the second karaoke data stream on a display unique to the second class participant is directed. The presentation of the common data elements, the exercise-related data elements, the first data stream and the second data stream may be synchronized.

16 Claims, 16 Drawing Sheets

(51) Int. Cl.
| | |
|---|---|
| *A63B 71/06* | (2006.01) |
| *G06F 19/00* | (2018.01) |
| *G06F 17/30* | (2006.01) |
| *G09B 19/00* | (2006.01) |
| *A63B 22/06* | (2006.01) |
| *A61B 5/024* | (2006.01) |
| *G06Q 50/00* | (2012.01) |

(52) U.S. Cl.
CPC ...... *G06F 17/3074* (2013.01); *G06F 19/3481* (2013.01); *G09B 19/003* (2013.01); *G09B 19/0015* (2013.01); *G10H 1/361* (2013.01); *G10H 1/365* (2013.01); *A61B 5/024* (2013.01); *A63B 22/0605* (2013.01); *A63B 2024/009* (2013.01); *A63B 2024/0081* (2013.01); *A63B 2071/065* (2013.01); *A63B 2071/0625* (2013.01); *A63B 2220/803* (2013.01); *A63B 2220/806* (2013.01); *A63B 2225/20* (2013.01); *A63B 2225/50* (2013.01); *A63B 2230/06* (2013.01); *A63B 2230/75* (2013.01); *G06Q 50/01* (2013.01); *G10H 2220/011* (2013.01); *G10H 2240/181* (2013.01)

(58) Field of Classification Search
CPC ...... A63B 2024/0081; A63B 2024/009; A63B 2071/0625; A63B 2071/065; A63B 2220/803; A63B 2220/806; A63B 2225/20; A63B 2225/50; A63B 2230/06; A63B 2230/75; G06F 17/3074; G06F 19/3481; G09B 19/0015; G09B 19/008; G10H 1/361; A61B 5/024; G06Q 50/01

USPC .......................................................... 84/610
See application file for complete search history.

(56) References Cited

U.S. PATENT DOCUMENTS

| | | | |
|---|---|---|---|
| 5,982,980 A | 11/1999 | Tada | |
| 6,074,215 A * | 6/2000 | Tsurumi | G10H 1/365 434/307 A |
| 6,118,064 A * | 9/2000 | Yamamoto | G09B 5/06 434/307 A |
| 8,907,195 B1 * | 12/2014 | Erol | G09B 5/06 84/609 |
| 2008/0184870 A1 | 8/2008 | Toivola | |
| 2009/0165634 A1 | 7/2009 | Mahowald | |
| 2009/0298028 A1 * | 12/2009 | Saunders | G09B 19/003 434/258 |
| 2015/0080072 A1 * | 3/2015 | Kim | A63F 13/213 463/7 |
| 2015/0306498 A1 * | 10/2015 | Tornqvist | H04L 67/10 463/36 |
| 2016/0021412 A1 * | 1/2016 | Zito, Jr. | H04N 21/251 725/13 |
| 2017/0046971 A1 * | 2/2017 | Moreno | G09B 19/00 |

OTHER PUBLICATIONS

Ellis, "Extracting information from music audio," Aug. 2006, Communications of the ACM, vol. 49, No. 8, pp. 32-37.
International Search Report and Written Opinion dated Jul. 7, 2016 in relation to PCT Application No. PCT/CA2016/050527, filed on May 6, 2016.

* cited by examiner

SUBSCRIBER                                                      70

| ID | NAME | PROFILE STATUS | SUBSCRIBER TYPE |
|---|---|---|---|
| 000001 | John Doe | Active | Individual |
| 000002 | Jane Doe | Active | Individual |
| 000003 | Don Smith | Inactive | Individual |
| 000004 | Bob White | Active | Individual |
| 100001 | GoodFun | Active | Facility |
| 100002 | University of Toronto Downtown | Active | Facility |
| 100003 | University of Toronto Mississauga | Inactive | Facility |

SUBSCRIBER_LICENSES                                             72

| ID | Licensed Workouts Registered | Licensed Workouts Remaining |
|---|---|---|
| 000001 | 1 | 9 |
| 000002 | 5 | 5 |
| 000003 | 4 | 6 |
| 000004 | 8 | 2 |
| 100001 | 10 | 10 |
| 100002 | 5 | 15 |
| 100003 | 19 | 1 |

SUBSCRIBER_SITES  /— 74

| ID | Facility 1 | Facility 2 |
|---|---|---|
| 000001 | YMCA TORONTO | YMCA OTTAWA |
| 000002 | GOODFUN | NIL |
| 000003 | TORONTO COMMUNITY CENTRE | NIL |
| 000004 | UNIVERSITY OF TORONTO DOWNTOWN | UNIVERSITY OF TORONTO MISSISSAUGA |

SUBSCRIBER_PREFERENCES  /— 76

| ID | Preferred Music | Preferred Social Networking App |
|---|---|---|
| 000001 | Dance | Facebook |
| 000002 | Disco | Twitter |
| 000003 | 80's Pop | Twitter |
| 000004 | Rock | Pinterest |

PACKAGE  /— 78

| ID | Spinging Exercise Package |
|---|---|
| 000001 | A |
| 000002 | C |
| 000002 | D |
| 000004 | [B,E] |
| 100001 | [A,B,C] |
| 100002 | [B,D,F] |
| 100003 | [A,B,C,D,E] |

CLASSES

| Class | Instructor | Date | Time | Exersing Exercise Package | Members Registered |
|---|---|---|---|---|---|
| Spinging Level 1 | Lucy | 05/01/14 | 13:00 | A | [001, 002] |
| Spinging Level 2 | Jean | 05/01/14 | 17:00 | B | [002, 004, 005] |
| Spinging Level 3 | Paul | 05/06/14 | 06:30 | C | [002, 004, 006] |

FIG. 9A

SUBSCRIBED_PACKAGES

| Spinging Exercise Package | Licensed Workouts Used | Licensed Workouts Remaining |
|---|---|---|
| A | 25 | 25 |
| B | 10 | 40 |
| C | 35 | 15 |

FIG. 9B

SYNCHRONIZED EXERCISING AND SINGING

FIELD OF THE INVENTION

The present invention relates to a computer-implemented application for creating, accessing, downloading and playing synchronized audio, video and instructions related to exercise routines for use during individual exercise sessions and group exercise classes. The invention relates to a range of exercise types including stationary cycling [a.k.a. spinning], aerobics and the like.

BACKGROUND OF THE INVENTION

Instructor-led group exercise classes have been popular for decades. For example, in the 1970's and 1980's aerobic classes, in which instructors led aerobic exercises set to music, gained widespread popularity. Over time, variations of group exercise classes abounded. Today, a wide variety of exercise classes making use of various types of equipment and set to various types of music—e.g. Zumba™ (dance) and Spinning™ (group stationary bicycle classes), Pump™ (Body countering with weights), Aerobics™ (step exercises)—are available and offered for personal and group use by DVD, Internet including YouTube and exercise facilities ranging from home gyms, to public or membership based gyms, to local YMCAs.

Although the type of music, physical movements and equipment used varies from class to class, most group exercise classes have in common the characteristics that they are instructor-led. Many are set to music. Some classes further incorporate music videos or other imagery to assist in motivation (e.g. videos of terrain in stationary biking classes). Thus, for example, in a Spinning class, typically, an instructor will play a playlist which either the instructor or a master distributor has compiled, e.g. a collection of popular songs with particular beat counts to set a particular pace for an exercise, over the classroom's sound system. The instructor may also choose to play a video showing popular cycling trails (e.g. the hills of Italy or routes through Napa Valley) to provide entertainment and motivation to class participants. It is also common in these classes for the instructor to call out commands (e.g. increase resistance to 70%, "position 1", "position 2", "freeze") from time to time. Instructors typically encourage class participants to sing along with the music as added motivation and as a group bonding exercise.

Typically, the primary emphasis of such exercise classes with music is unquestionably exercise. While the music is important, it is secondary to the exercise with little or no effort made to facilitate it.

A drawback of group exercise classes is that typically the music and/or videos are broadcast to the entire class and everyone experiences the same music and same video and not all class participants may be familiar with the melody or lyrics to the songs. This may make it difficult for class participants to sing along. Notably, karaoke systems, which allow users to sing along with songs by scrolling the lyrics to songs in synchrony with the music across a screen, are widely known and popular. Heretofore, singers have typically enjoyed the karaoke experience in karaoke bars or at home; however, it would be quite enjoyable for singers to be able to enjoy karaoke during group exercise classes as well.

SUMMARY

System and methods for offering and facilitating synchronized singing during an individual or group exercise session are provided. More specifically, exercise routines incorporating synchronized singing during individual and group exercise classes, providing words, music and/or video integrated with individual exercise monitors and information is provided.

In accordance with the present disclosure, there is provided a computer-implemented method for facilitating a karaoke performance while exercising during an individual exercise session or group exercise class, comprising receiving an indication of a song to be performed during said session or exercise class; retrieving at least one computer-readable karaoke file corresponding to said song, wherein said at least one computer-readable karaoke file comprises common data elements, at least two independent karaoke data streams and exercise-related data elements; receiving from a first class participant a selection of a first data stream of said at least two independent karaoke data streams; receiving from a second class participant a selection of a second data stream of said at least two independent karaoke data streams; directing the presentation of said common data elements and said exercise-related data elements on a display common to said first and said second class participants; directing the presentation of said first karaoke data stream on a display unique to said first class participant; and directing the presentation of said second karaoke data stream on a display unique to said second class participant, wherein the presentation of said common data elements, said exercise-related data elements, said first data stream and said second data stream are synchronized.

In accordance with an aspect of the present disclosure there is provided a system for providing and managing access to karaoke files for use during individual and group exercise routines, comprising a first computing device hosting a memory storing a plurality of computer-readable karaoke files adapted for use during individual and group exercise classes, wherein each of said karaoke files comprise common data elements, at least two independent data streams and exercise-related data elements; a plurality of exercise class participants, each in communication with said first computing device over a communications network, each stationary bike further hosting an application directing the selective presentation of data on a display of said bike; a second computing device in communication with said plurality of stationary bikes and said first computing device, said second computing device hosting an application directing the presentation of said common data elements and said exercise-related data elements on a display common to all class participants and the presentation of certain selected independent data streams on the displays of certain monitors of said plurality of monitors.

The purpose of the invention is to facilitate singing while exercising. The invention achieves this by providing the words and music for singing purposes coupled to synchronized exercise instructions.

The basic level of singing while exercising involves a single participant (or all participants in a group exercise class) singing along to the music piece. The advanced levels include an option to provide the words and music for multiple parts e.g. soprano, alto, tenor and bass to facilitate singing harmonies etc.

The health and other benefits of singing while exercising are numerous and include:
  a) raising a participant's heart rate several beats above exercising only levels
  b) increased enjoyment and, consequently, motivation to participate c) having fun and creating a sense of well-being. Singing alone is liberating, and good for the body and soul d) combining exercising and singing significantly increases the market for exercise classes at facilities. Typically gymnasiums attract hard-core "gym junkies" whose primary focus is keeping in shape and accordingly go for the exercise. For members other than "gym junkies" gyms struggle to attract and retain members. The typical turnover/dropout rate is high. By offering a different style of exercise, where having fun and enjoying music together is as important as keeping in shape, although that will "painlessly" occur in parallel, the gyms significantly increase the number of prospective members.

Singing while exercising with a group is fun and social. Making music with others creates a bond and increases the opportunity for and encourages social interaction. Accordingly, the invention recognizes and facilitates the social opportunities.

The invention recognizes and protects the composers', musicians' and music publishers' intellectual property rights and ensures royalties are accounted for and paid.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate by way of example only, embodiments of this invention:

FIGS. 7A-7F illustrate an exemplary schema of the subscriber database of FIG. 1;

FIGS. 9A and 9B illustrate an exemplary schema of the facility database of FIG. 1;

DETAILED DESCRIPTION

Figure 1:
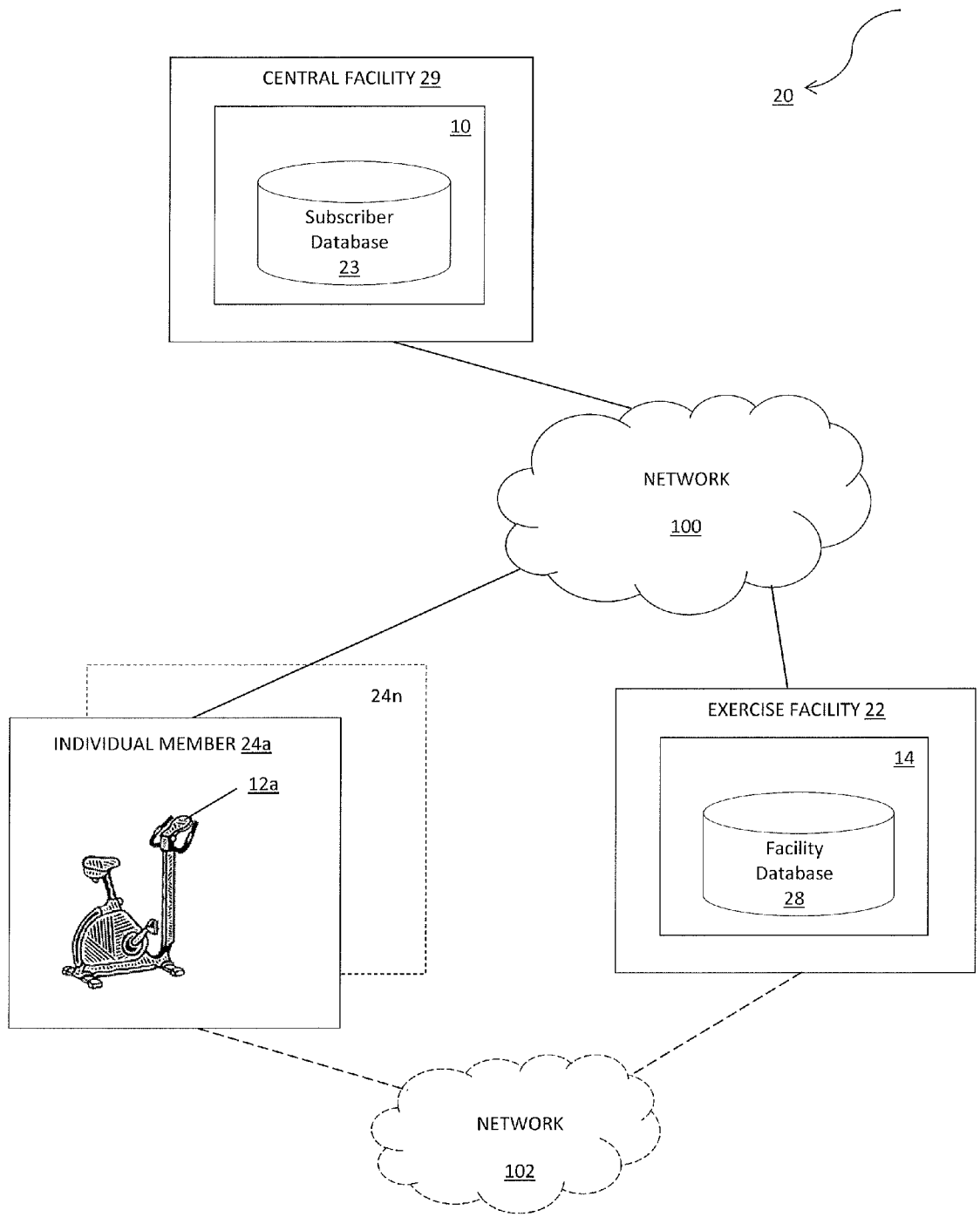
FIG. 1 is a block diagram of a system, including a central subscriber database that stores pre-programmed exercise routines for use in an exercise and singing ("exersing") application, exemplary of an embodiment of the present application.

FIG. 1 depicts an example system 20, which may provide an "exercise" and sing ("exersing") service, exemplary of an embodiment of the present invention. For illustration purposes, "exersing-spin" ["spinging"] is used as an example. In particular, the "exersing" service may be a subscription-based service allowing access to stationary bike routines ("spinging" routines) and other types of exercise and sing routines e.g. "exersing-dance", "exersing-aerobics" which may be created and maintained by a central provider ("exersing" service provider). E.g. subscribing individual members and/or fitness facilities offering such stationary bike classes may subscribe to and download "spinging" routines from the "exersing" service provider.

The "exersing" service provider, in addition to providing the "exersing" service, may itself create the "exersing" routines e.g. "spinging" routines for distribution to subscribers of the "exersing" service. In particular, and as will be further explained below, the "exersing" service provider may itself create composite files made up of multiple audio, video, music, text, graphic and animation elements which files may be packaged to form the "exersing" routines that are distributed to subscribers of the "exersing" service. Advantageously, these "exersing" routines may allow "exersing" class participants to sing along with the music during the exercise class in karaoke fashion.

More particularly, central facility 29 may be a physical location, for example, an office, which houses central facility computer system 10. Central facility computer system 10 may host subscriber database 23 which, as further detailed below, may contain subscriber user records and a selection of exercise routines available to be downloaded. Exercise facility 22 may be a physical location, for example, a fitness facility which houses an exercise facility computer system 14. Exercise facility computer system 14 may host facility database 28. System 20 may further include individual computing device 12, which may conveniently be a computer system integrated with a piece of exercise equipment such as a Spinning bike. Computing device 12 may also be a smartphone or tablet capable of receiving data and displaying information such as participant heart rate, rpms and resistance levels from a stationary bike, heart rate monitor etc capable of transmitting the required data. As required, computing device 12 may be in communication with one or more biometric monitors—e.g. a pulse rate monitor, or the like—in order to receive an indication of physical exertion, calories burned, etc. by a participant. Computer systems/device 10, 12 and 14 may be interconnected by network 100. Network 100 may be a wide area network, local area network or a combination thereof, and may be wired or wireless. Exercise facility computer system 14 and bike 12 may optionally be interconnected via network 102, which may be, for example, a wireless network (e.g. one conforming to the IEEE 802.11g protocol) operated by exercise facility 22 and to which device(s) 12 may connect to while on the premises of exercise facility 22 or while within range of wireless network 102. Conveniently, network 100 may be the Internet. Thus, for example, in an exemplary embodiment of the present application, facility computer 14 may connect to central facility computer system 10 via the internet to download "exersing" routine packages onto facility computer system 14. When onsite, for example, in preparation for or during an exercise class at exercise facility 22, individual member 24 using his or her bike/computing device 12 may connect to facility computer system 14 to download or access a given "exersing" routine package.

Notably, and as shown in FIG. 1, individual member 24 may be a plurality of members of exercise facility 22 (e.g. members 24a, . . . , 24n—collectively and individually member(s) 24), whose information may be stored in facility database 28. In an exemplary embodiment of the present application, and as further detailed below, members 24a, . . . , 24n may be members of a group stationary bike class (e.g. Spinning class) provided by exercise facility 22. Members 24a, . . . , 24n may (optionally) sign up for a given Spinning class via their respective computing devices 12a, . . . , 12n—collectively computing devices 12. Preferably, computing device(s) may be integrated into the Spinning (exercise) bike but may also be, for example, a tablet or smartphone which may communicate with the Spinning bike. Spinning bikes either with integrated computing systems and internet/network connectivity, or which are capable of communicating with external devices such as tablets or smartphone are known. Spinning bikes with integrated computer systems exist e.g. http://www.proform.com/fitness/en/ProForm/Exercise-Bikes/Tour-De-France-Pro.

Members 24 and their computing devices 12 and bikes may be co-located at a single gym or similar location. Alternatively, one or more members 24 and computing devices 12 may be at a remote location, distant from the remaining device 12, and interconnected by a computing network 100, as further described below.

Figure 2:
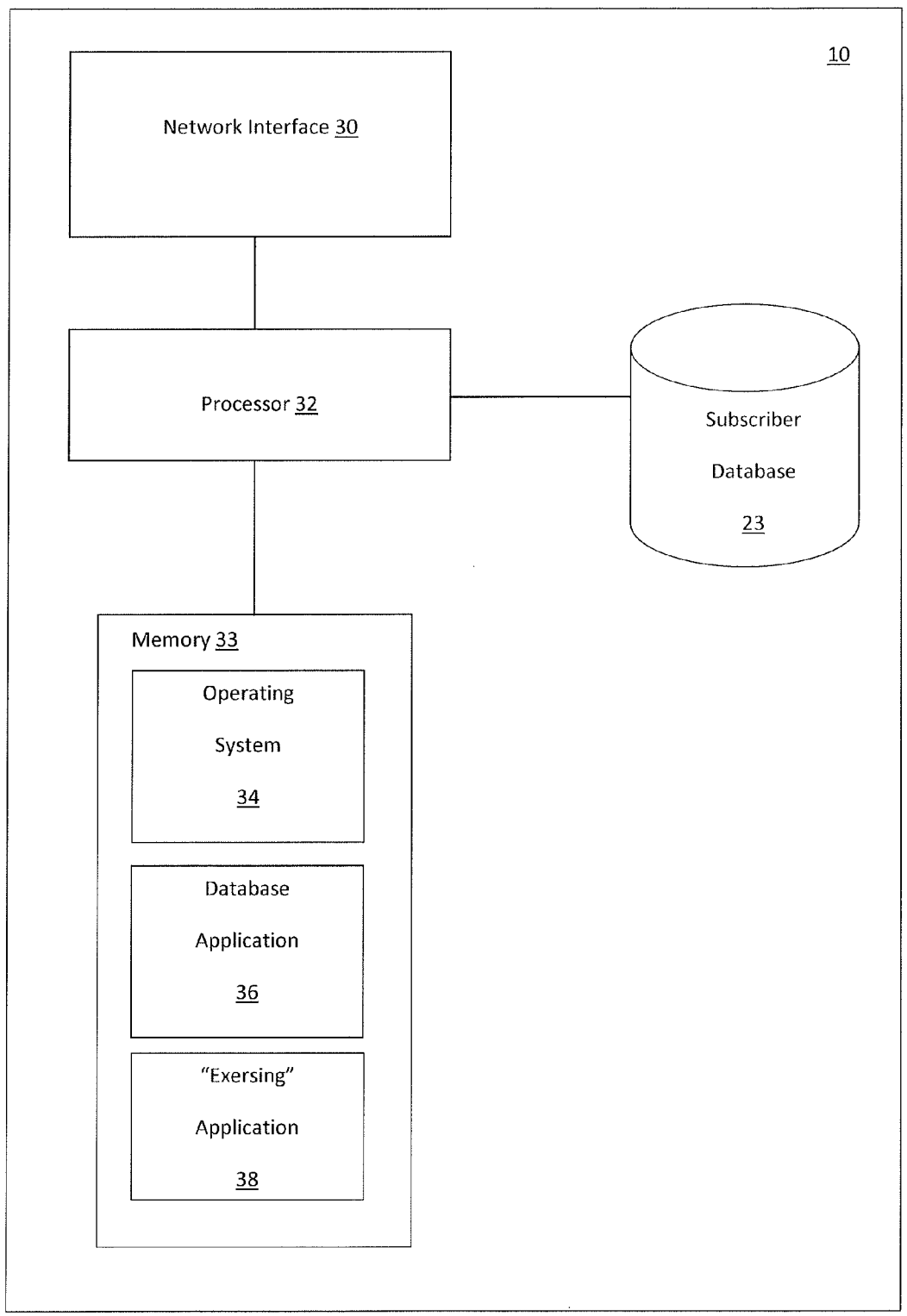
FIG. 2 is a block diagram depicting the contents of temporary and persistent memory storage of a computer system hosting the central subscriber database in the system of FIG. 1.

As illustrated in FIG. 2, central facility computer system 10 may be a conventional computer having a processor 32, a network interface 30, memory 33 hosting operating system 34 (e.g. Windows 8, Linux, Mac OS) and a database application 36. Memory 33 may also host "exersing" application 38, an exemplary embodiment of the present application, as further explained below. Central facility computer system 10 may also host subscriber database 23, containing records of individuals and/or fitness facilities which subscribe to the "exersing" service. Database application 36 may be a conventional relational database management system for managing subscriber database 23, for example, Oracle™ or Microsoft SQL Server, which may conveniently include a web interface. Processor 32 may execute operating system 34, database application 36, "exersing" application 38 and other applications (not shown). Network interface 30 may be any conventional piece of hardware used to interface central facility computer system 10 with network 100, for example, an Ethernet card, to allow central facility computer system 10 to communicate over network 100.

Figure 3:
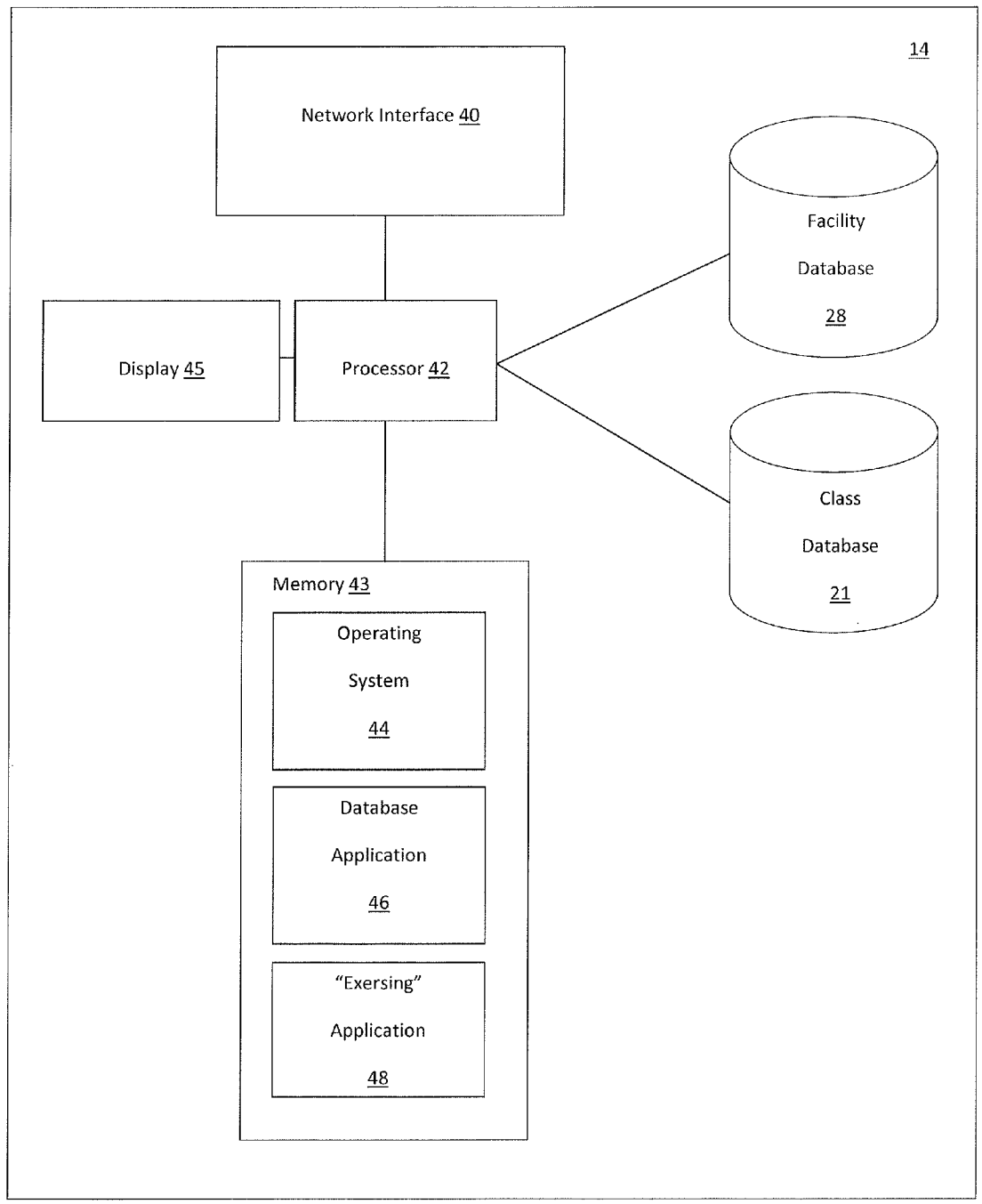
FIG. 3 is a block diagram depicting the contents of temporary and persistent memory storage of a computer system hosting the facility database in the system of FIG. 1.

FIG. 3 is a block diagram of exercise facility computer system 14. Exercise facility computer system 14 may be a conventional computer (e.g. PC) located onsite at exercise facility 22, which may include network interface 40 (e.g. Ethernet card), processor 42 and memory 43. Exercise facility computer system 14 may further host facility database 28. As will be further explained below, facility database 28 may include records of registered members of exercise facility 22 and records relating to the types, dates and times of various exercise classes being offered by exercise facility 22. Conveniently, facility database 28 may further include records of "exersing" packages licensed from the "exersing" service provider, and in particular may be used to track the number of licensed workouts used and number of licensed workouts remaining.

Similar to central facility computer system 10, memory 43 of exercise facility computer system 14 may include operating system 44 (e.g. Windows 8, Mac OS), database application 46 and "exersing" applications e.g "spinging", "exersing-dance". Database application 46 may be a conventional relational database management system for managing facility database 28. Exercise facility computer system 14 may further include display 45 on which graphical elements relating to the "exersing" application, and in particular, relating to a particular "exersing" package e.g "sping", may be displayed. An exemplary screenshot depicting such graphical elements is provided in FIG. 5. Notably, "exersing" application 48 may be the client-side of "exersing" application 38 hosted on central facility computer system 10. "Exersing" application 48 may be, for example, downloaded from central facility computer system 10 and installed on exercise facility computer system 14 upon initial registration with the "exersing" service provider.

Figure 4:
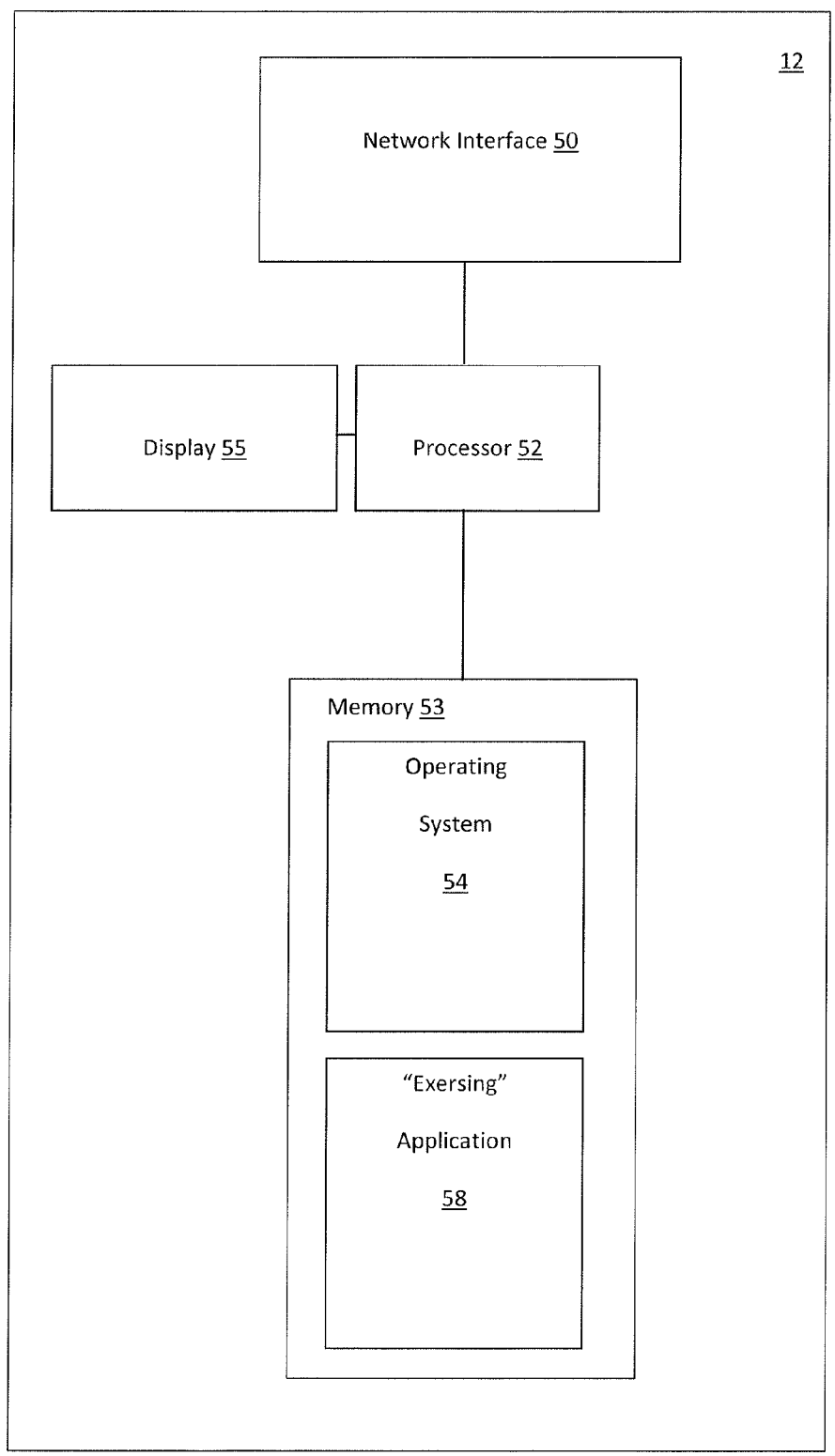
FIG. 4 is a block diagram depicting the contents of temporary and persistent memory storage of an individual member's computer system hosting an application exemplary of an embodiment of the present applicant, in the system of FIG. 1.

Referring to FIG. 4, an individual may access the "exersing" service, exemplary of an embodiment of the present application, using his or her personal computing device 12. In the primary embodiment of the present application, computing device 12 may be integrated into a piece of exercise equipment (e.g. stationary exercise bike). Alternatively, computing device 12 may be any form of conventional computing device, including, conveniently, a portable device such as a tablet or smartphone (e.g. iPad, iPhone, BlackBerry, Android) which may be used by a member 12 while onsite at exercise facility 22 to download, access and run a particular "exersing" package during e.g. a scheduled Spinning class. Additionally, if not integrated into the exercise bike, computing device 12 may be connectable to the exercise bike and may receive data transmitted from the exercise bike such as rpms and resistance levels and/or a biometric device such as a heart rate monitor.

Figure 6:
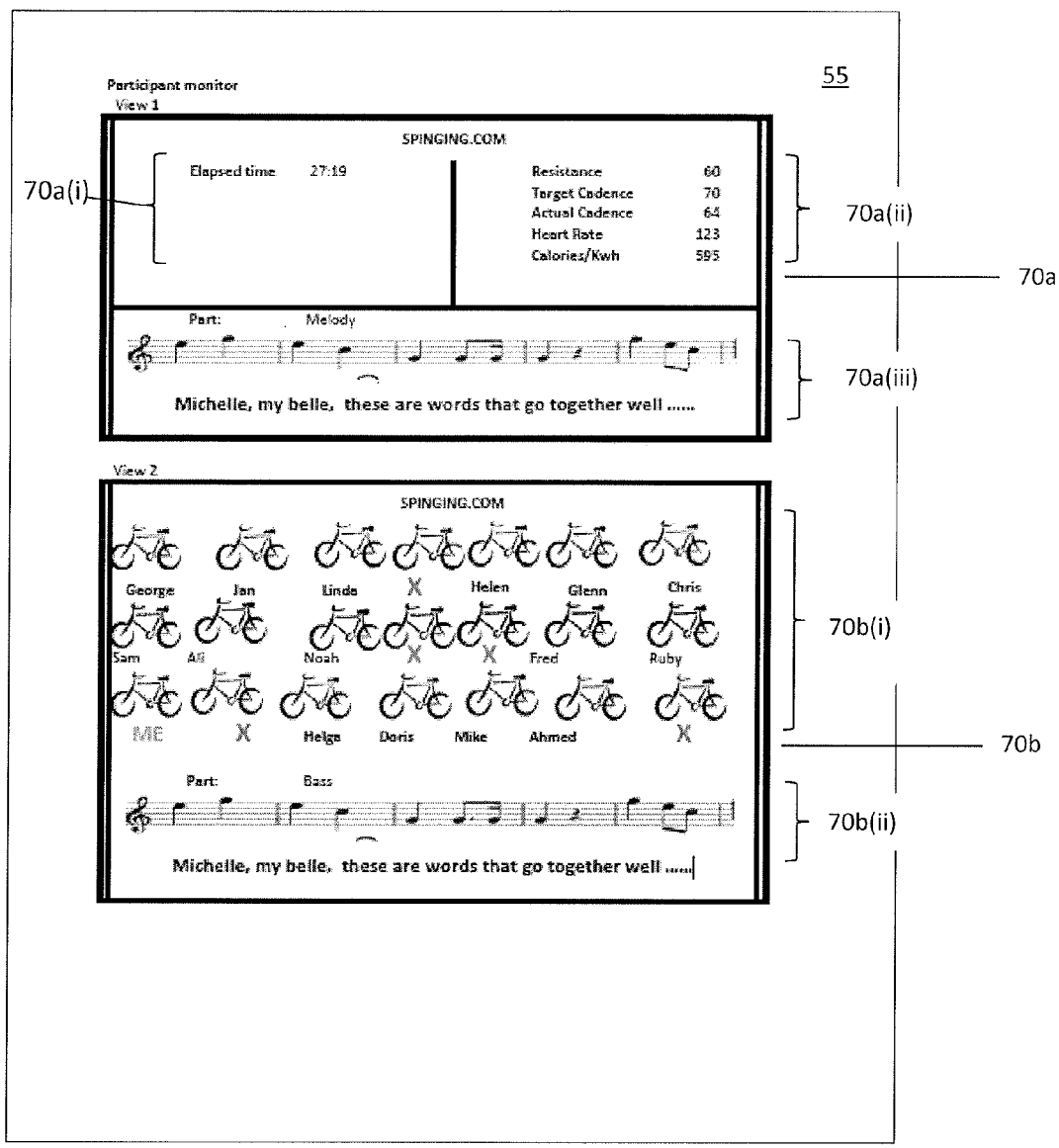
FIG. 6 is an exemplary screenshot of a screen of the "spinging" application displayed on the display of the computer system of FIG. 4.

Computing device 12 may include a network interface 50 allowing device 12 to interface with (wireless) network 102 (or network 100) and may further include processor 52 and memory 53. Memory 53 may host operating system 54 (e.g. iOS, Android, Windows Phone) and "exersing" application 58. An exemplary screenshot of such elements is depicted in FIG. 6. Similarly, "exersing" application 58 may be the client-side of "exersing" application 38 hosted on central facility computer system 10. "Exersing" application 58 may be, for example, downloaded from central facility computer system 10 and installed on exercise facility computer system 14 upon initial registration with the "exersing" service provider.

Moreover, computing device 12 may include display 55, which may be a touch screen display, for displaying graphics related to "exersing" application 58, and more particularly, elements of the "exersing" package selected by the particular individual for display during a scheduled exercise class. Notably, since each individual class participant is running his or her own version of "exersing" application 58, although all class participants are following the same "exersing" exercise package, each person may select the elements of the package (e.g. instrumentals only, sheet music for soprano part of song, etc.) that he or she wishes to see or hear. Thus, in effect, each participant may experience a customized version of the common "exersing" exercise package.

Conveniently, central facility computer system 10, exercise facility computer system 14 and personal computing device 12 may communicate with each other via the "exersing" applications 58 installed on the respective devices. In an alternate embodiment of the present application, the "exersing" service provider may sell "exersing" applications 48 and 58 on an online app store such as iTunes (e.g "Spinging app"). Users wishing to subscribe to a specific "exersing" service e.g. "spinging" may purchase the "spinging" application 58 from the online service in the conventional manner and thereby join and access the "spinging" service.

More specifically, participants whether they be individual users [e.g. that exercise alone e.g. at home] or group class participants may register online with the central facility computing system 10. Once registered, participants may purchase and download an "exersing" file/song; or purchase and download an "exersing" session including several files/songs (analogous to purchasing an album of songs). Optionally, participants could possibly register and pay for future "exersing" class or classes at a licensed "exersing" facility. Scheduled "exersing" classes at the "exersing" members "favourite" licensed "exersing" facility and/or nearby licensed "exersing" facilities may, for example, be visible using the "exersing" app. The central facility computing system 10 may further notify the licensed "exersing" facility's system each time a member registers and pays for "exersing" class or classes at the facility. The central computer system 10 may provide numerous flexible options for both distributors, facilities, instructors and individuals (whether they be participating as part of an organized group at a facility or alone) in order to provide "exersing" content.

Figure 7F:
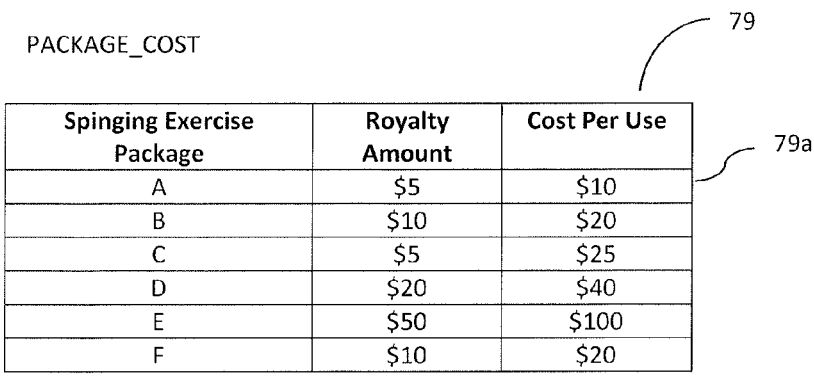

An exemplary schema of subscriber database 23 is outlined and described in FIGS. 7A-7F. In particular, FIG. 7A shows an exemplary SUBSCRIBER table 70 which contains records of individual members and fitness facilities which have subscribed to the "exersing" service. SUBSCRIBER table 70 contains the following attributes: "ID", "NAME", "Profile Status" and "Subscriber Type". In this exemplary SUBSCRIBER table 70, the "ID" attribute is the primary key. The value of the "Name" attribute may be used to store the name of an individual subscriber or name of a fitness facility subscriber. The value of the "Profile Status" attribute may be either "Active" or "Inactive" and the value of the "Subscriber Type" attribute may indicate whether the subscriber is an individual or a facility. Records 70a-70d correspond to individual subscribers and records 70f and 70g correspond to facility subscribers.

More specifically, record 70a is a record related to an individual active subscriber named "John Doe". Record 70c corresponds to an inactive individual subscriber named "Don Smith". Record 70e corresponds to a facility active subscriber, "GoodFun".

Thus, for example, as a facility subscriber, GoodFun may access and download "exersing" routines for use during group stationary bike exercise classes offered in its facilities. In contrast, an individual subscriber may access and download "exersing" routines onto his or her personal computing device (e.g. tablet, or internet-enabled exercise equipment) and may thereby conveniently follow the routine individually and at his or her own leisure, without the need to attend a group class. As may be appreciated, this provides increased flexibility to an individual subscriber—for example, the individual subscriber may exercise at a time and place convenient to him or her but still enjoy the benefit of following a licensed "exersing" exercise package.

FIG. 7B shows an exemplary SUBSCRIBER_LICENSES table 72 which indicates the number of licensed workouts registered by a subscriber and the number of licensed workouts remaining. For example, row 72a indicates that subscriber with ID 000001 (i.e. "John Doe", as determined by joining SUBSCRIBER_LICENSES table 72 with SUBSCRIBER table 70) has a total of 10 licensed workouts and of these, he has registered 1 licensed workout (i.e. used up 1 licensed workout) and has 9 licensed workouts remaining. Similarly, row 72b indicates that GoodFun has licensed a total of 20 workouts, has used 10 of these, and has 10 remaining.

FIG. 7C is an exemplary SUBSCRIBER_SITES table 74 which stores information about the facilities where individual subscribers attend group exercise classes. For example, row 74a indicates that subscriber "John Doe" (as determined by joining SUBSCRIBER_SITES table 74 with SUBSCRIBER table 70) attends YMCA Toronto (Facility 1) and YMCA Ottawa (Facility 2).

FIG. 7D is an exemplary SUBSCRIBER_PREFERENCES table 76 which includes records indicating each user's preferred music and preferred social networking app preferences. So, for example, row 76a indicates that subscriber "John Doe's" preferred music is "dance" and his preferred social networking app is "Facebook", and row 76b indicates that subscriber "Don Smith" prefers "80's pop" and his preferred social networking app is "Twitter". Information about such preferences, may be used to, for example, present a user with a list of suggested packages (in the case of John Doe, packages containing dance music) and/or send John Doe updates through Facebook.

FIGS. 7E and 7F shows exemplary PACKAGE table 78 and PACKAGE_COST table 79, respectively. More specifically, PACKAGE table 78 indicates which "exersing exercise package" (i.e. package A, B. C, D, E or F) each subscriber has subscribed to. Thus, as indicated by exemplary record 78a, subscriber ID 000002 (i.e. "Jane Doe") has subscribed to package C; subscriber ID 100001 (i.e. GoodFun) has subscribed to packages A, B and C (as indicated by record 78b); and subscriber ID 100003 (i.e. University of Toronto Mississauga) has subscribed to packages A, B, C, D and E (as indicated by record 78c). As may be appreciated, each package may be in the form of a computer readable file format recognized by "exersing" applications 38, 48 and 58.

More specifically, each package may comprise a playlist of multiple songs. For example, package A may be a 45-minute exercise routine which includes a playlist of 12 songs each with an average playtime of approximately 4 minutes. Conventionally, the playlist would simply consist of 12 songs and the songs would be played one after another during the exercise class. However, and in accordance with the present application, each package A-F may include other elements such as: sheet music corresponding to each song in the playlist; lyrics to the song; sheet music corresponding to different vocal parts of the song (e.g. soprano, alto, tenor and bass parts); instrumental part only of the song; music video related to the song; text instructions ("position 1", "70% resistance level", "100 rpm", etc.); overdubbed instructions (e.g. "position 1", "70% resistance level", "100 rpm", etc.); and information transmitted on the fly from the bike or external devices (e.g. heart rate, calories burned). Of course, elements other than those described may be included in an exercise package file. As will be further described below, the user may selectively turn each of the aforenoted elements "on" and "off". Thus, for example, the user may select to have only the instrumental part of the song and text instructions play, but not music video, overdubbed instructions, or any of the other elements.

The cost of each of packages A-F may be stored in exemplary PACKAGE_COST table 79 (FIG. 7F). In particular, table 79 may store information about the cost per use of each package and the amount of royalties to be paid on each package, to, for example owners of copyrighted materials in those packages (e.g. royalties to be paid to the artists of the songs included in each package). Thus, for example, record 79a indicates that exercise package A costs $10 per use (i.e. a subscriber is charged $10 per license for package A) and $5 of royalties are payable per use of package A.

Central facility 29 may manage, administer and account for the acquisition of licenses of the copyrighted content (e.g. songs, music, video, etc.) and associated payment of royalties to the authorized agencies. (e.g. SOCAN in Canada). Such centralized administration and accounting may ensure compliance and minimize leakage.

Of course, other schemas of subscriber database 23, containing other types of tables, records and attributes, may be employed and would be apparent to those of ordinary skill in the art.

Figure 8:
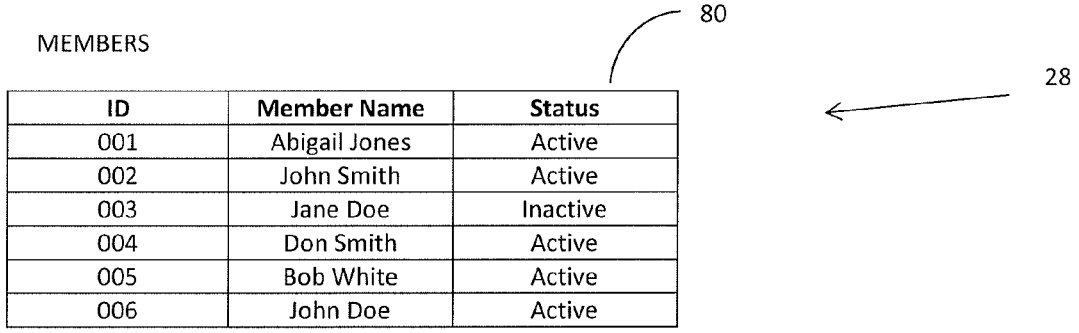
FIG. 8 illustrates an exemplary table of the facility database of FIG. 1.

Returning to FIG. 1, facility database 28 may contain information regarding members of exemplary exercise facility 22. Exemplary MEMBERS table 80 of facility database 28 is shown in FIG. 8. Specifically, table 80 has six records, each corresponding to a member of exercise facility 22. Each of these members may, in the conventional fashion, check into exercise facility 22, e.g. by swiping their membership card through a card reader of exercise facility 22, and computer system 14 may verify that that member is in fact a member (or an active member) of exercise facility 22 by querying MEMBERS table 80 of facility database 28. Of course, other schemas of facility database 28, containing other types of tables, records and attributes, may be employed and would be apparent to those of ordinary skill in the art.

Exemplary CLASSES table 90 and SUBSCRIBED_PACKAGES table 92 which may be part of facility database 28 of exercise facility 22 is shown in FIGS. 9A and 9B. As shown, CLASSES table 90 may contain records 90a, 90b and 90c, each corresponding to a different spinning class. For example, record 90a provides that "Spinging Level 1" class is scheduled to occur on May 1, 2014 at 13:00 hours (i.e. 1 pm) and taught by instructor "Lucy". Moreover, record 90a indicates that "Spinging package A" will be used during the class and that members with ID's 001 (i.e. "Abigail Jones") and 002 (i.e. "John Smith") (see MEMBERS table 80) have signed up/registered for the class.

Referring to FIG. 9B, SUBSCRIBED_PACKAGES table 92 may track the number of licensed workouts used up by exercise facility 22 and number of licensed workouts remaining. Accordingly, exemplary record 92a indicates that exercise facility 22 has used up 25 licenses for "Spinging package A" and has 25 licenses remaining.

Of course, other schemas of facility database 28, containing other types of tables, records and attributes, may be employed and would be apparent to those of ordinary skill in the art.

Figure 10A:
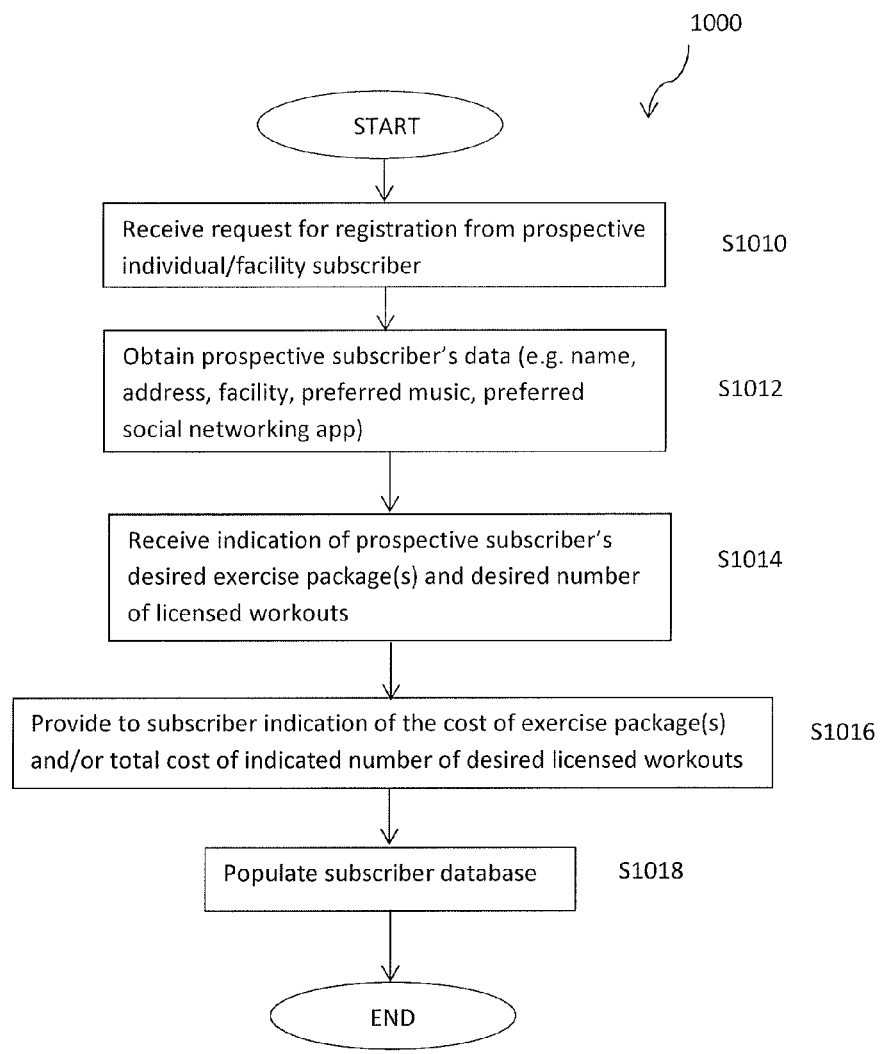
FIG. 10A is a flow diagram illustrating the operation of the computer system of FIG. 2 upon receiving a request for registration for the "exersing" application exemplary of an embodiment of the present application.

Operation of system 20, exemplary of an embodiment of the present application, will now be described with reference to FIGS. 10-12.

Flow diagrams 1000 (FIG. 10A) and 2000 (FIG. 10B) describe operation of central facility computer system 10, more specifically, registration of an individual subscriber or facility subscriber for access to the "exersing" service of the present application. To begin, central computer system 10, specifically, "exersing" application 38 running on central computer system 10, may receive a request for registration from a prospective individual or facility subscriber (S1010). This request may, for example, be sent from "exersing" application 58 hosted on the individual's computing device 12, or from "exersing" application 48 hosted on exercise facility computer system 14. "Exersing" application 38 may next request and obtain the prospective subscriber's data, for example, name, address, facility or facilities frequented, preferred music and preferred social networking app (S1012). Then, "exersing" application 38 may receive an indication of the prospective subscriber's desired exercise package(s) (e.g. "exersing package A") and desired number of licenses (e.g. 10 licenses) (S1014). Based on this information, "exersing" application 38 may query subscriber database 23, in particular, PACKAGE_COST table 79 (FIG. 7F) to determine the cost of the selected package(s) and return to the prospective subscriber an indication of the cost of the selected exercise package(s) (S1016). For example, supposing the prospective subscriber indicates that she/he/it wishes to subscribe to 10 licenses to "exersing package E", e.g. "spinging", application 38 would return an indication of the total cost of $1000 (10×$100). "Exersing" application 38 may then request a credit card number to which the $1000 can be charged (not shown in FIG. 7F). Alternatively, other forms and methods of payment e.g. PayPal, electronic funds transfer, etc. may be accepted. Lastly, "exersing" application 38 may create new record(s) corresponding to the new member/subscriber in subscriber database 23 (S1018). Thereafter, the subscriber may be considered to be properly registered in system 20 and permitted to access and/or download "exersing" packages to which he/she/it has paid for.

Figure 10B:
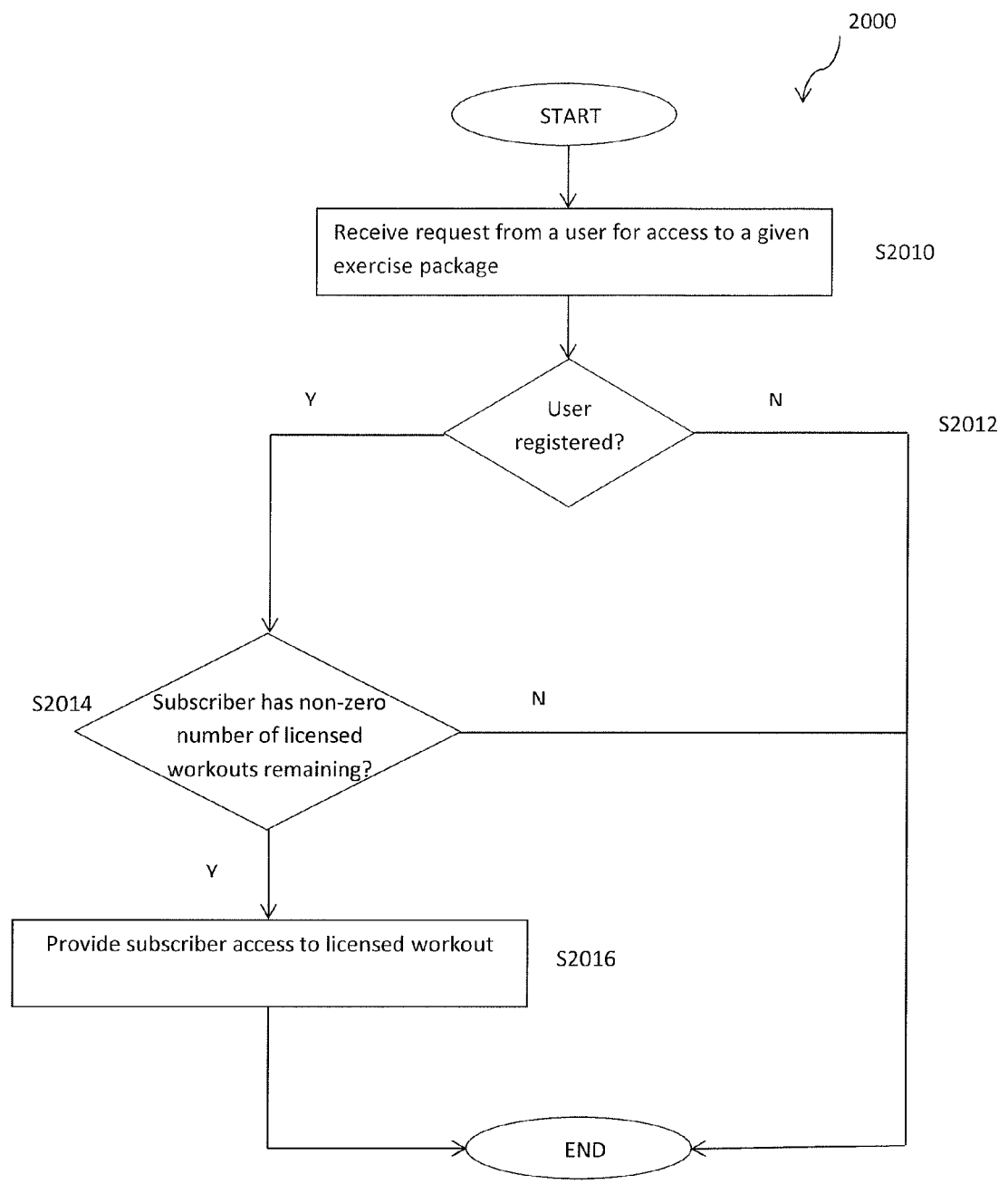
FIG. 10B is a flow diagram illustrating the operation of the computer system of FIG. 2 upon receiving a request to access the "exersing" application exemplary of an embodiment of the present application.

Operation of central computer system 10 upon receipt of a request from a subscriber is illustrated in flow diagram 2000 (FIG. 10B). Upon receiving a request from a user for access to a given exercise package (S2010) "exersing" application 38 running on central computer system 10 may query subscriber database 23 to determine whether the user is registered (S2012). If the user is not registered, then "exersing" application 38 will deny access (or alternatively, present an option allowing the user to register). If the user is registered, then "exersing" application 38 may further query subscriber database 23 to determine whether that user has a non-zero number of licensed workouts remaining (S2014). If so, then the user may be permitted to access or download a copy of the "exersing" package which he/she/it has licensed (S2016). Following the user's access or download, subscriber database 23, more specifically, SUBSCRIBER_LICENSES table 72 may be updated accordingly. As may be appreciated, the operations described in flow diagrams 1000 and 2000, and in particular, the operations requiring input and output to the user, may be presented via a conventional graphical user interface (GUI) (not shown).

As explained above, facility subscribers may, after obtaining and paying for licenses to particular "exersing" packages, use those packages during group exercise classes offered by the facility. Advantageously, the subscribing facility may install "exersing" application 48 e.g. "spinging" on each of its exercise bikes so that each participant in the facility's group exercise class may customize the "spinging" package to include or exclude elements as desired.

Alternatively, the facility may allow the simultaneous upload/download/transmit of a temporary file of the session's "exersing" program/package to all participants thereby ensuring all participants are playing the same songs in sequence and the timing of the songs being played at any time is synchronized.

Figure 11:
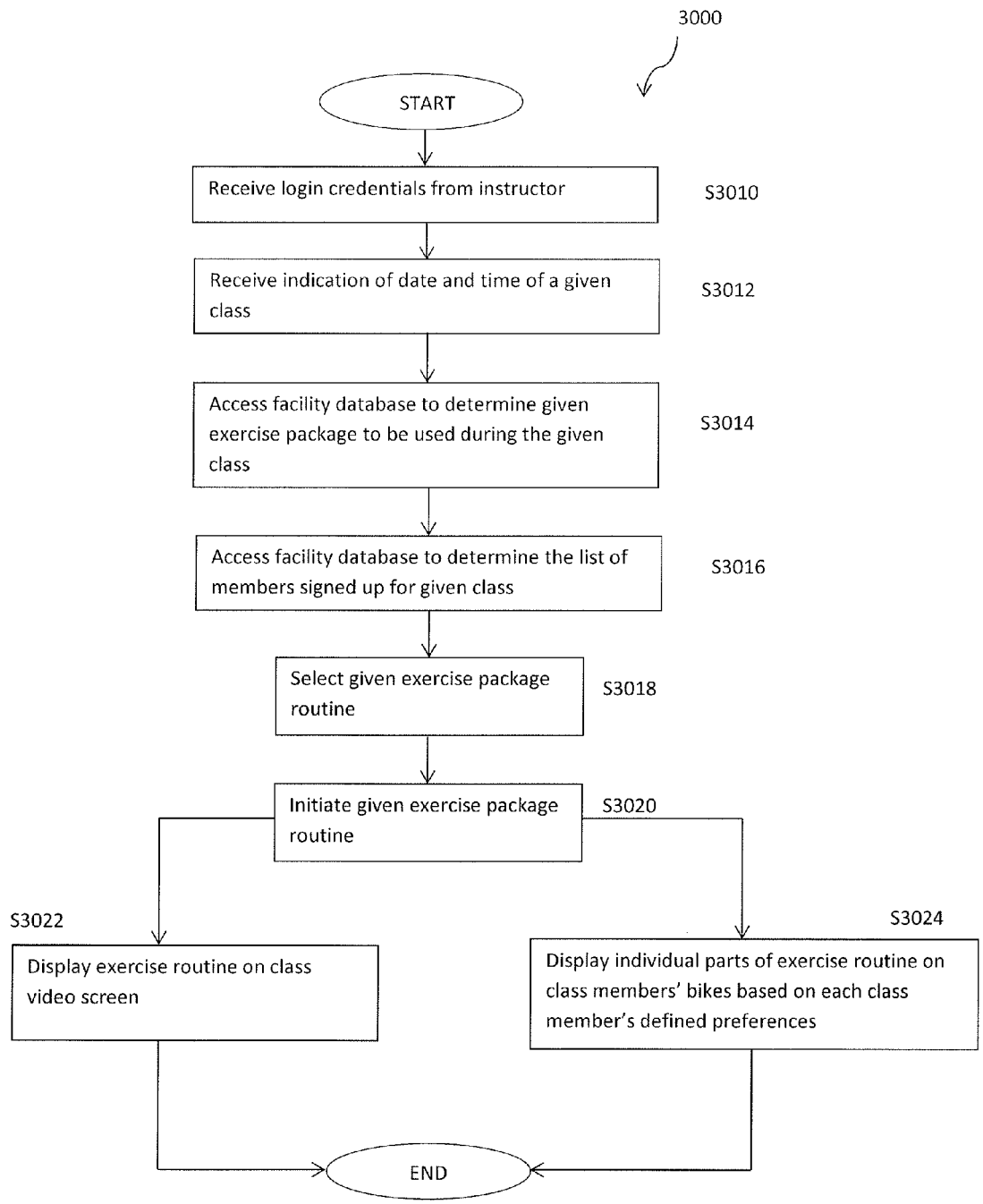
FIG. 11 is a flow diagram illustrating the operation of the computer system of FIG. 3 upon initiation of the "exersing" application exemplary of an embodiment of the present invention during a Spinning class.
Figure 12:
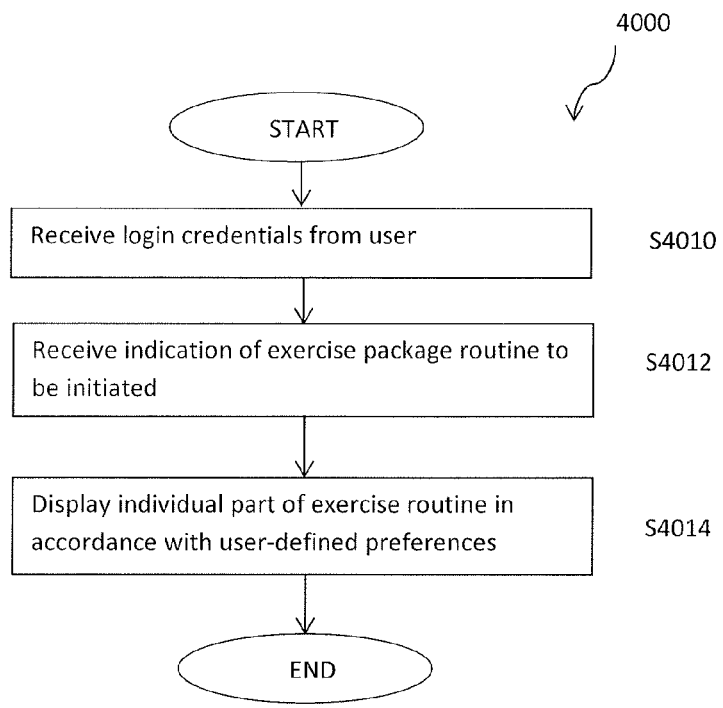
FIG. 12 is a flow diagram illustrating the operation of the computer system of FIG. 4 upon initiation of the "exersing" application exemplary of an embodiment of the present invention during a Spinning class.

FIG. 11 is a flow diagram 3000 which illustrates operation of exercise facility computer system 14, and more specifically, illustrates the use of an "exersing" exercise package during a group exercise class. To begin, "exersing" application 48 running on exercise facility computer system 14 may receive login credentials from an instructor (S3010). For example, and with reference to CLASSES table 90 (FIG. 9A), row 90a, on May 1, 2014 in preparation for the 1 pm "Spinging Level 1" class, instructor "Lucy" may log into "exersing" application 48 running on exercise facility computer system 14, from, for example, a computer or device located in the exercise room which is connected to computer system 14 via, for example, wired or wireless network 102. Instructor Lucy may next provide an indication of a date and time of the class (i.e. May 1, 2014 and 1 pm, respectively) (S3012). With this information, "exersing" application 48 may query facility database 28 to determine the exercise package to be used during the class (S3014) (i.e. package "A") and further to determine that list of members signed up for the class (S3016) (i.e. members with ID 001 ("Abigail Jones") and 002 ("John Smith")). In particular, assuming that someone authorized by exercise facility 22 (e.g. an employee of exercise facility 22) has previously downloaded package "A" from central facility 29, and the package "A" file is already stored on a computer readable medium connected to or accessible by facility computer system 14, package "A" may be selected (S3018), and initiated (S3020).

At this point, notably, instructor Lucy may select, via a GUI of "exersing" application 48 (for example, see FIG. 13) which audio/visuals and other elements related to "exersing package A" to present on the class video screen and/or sound system (S3022). Simultaneously, customized parts of the routine of "exersing package A" may be streamed to and displayed on Abigail Jones' and John Smith's individual devices (e.g. their stationary bike console screens) (S3024). Alternatively, Abigail and John's bikes may access a copy of package "A" stored on exercise facility computer system 14 via network 100 or 102. Significantly, the audio/visuals presented on the class video screen/sound system may be elements common to both Abigail and John (e.g. a video of climbing hills); however, the elements displayed on Abigail's individual screen may be customized to her preferences (e.g. sheet music corresponding to the soprano part of the song) and likewise for John (e.g. sheet music corresponding to the bass part of the song).

In order to keep all class participants in synchrony, exercise facility computer system 14 may act as the "master" and the class participant's bikes as the "slaves". More specifically, "exersing" application 58 may transmit timing information to exercise bikes 12 (via network 100 or 102) so that the participants' displays may be synchronized. In this manner, for example, John's music lyrics for the bass part may scroll across his bike console screen at the same rate as Abigail's sheet music for the soprano part is scrolling across her bike console screen. As may be appreciated, this allows John and Abigail to sing their respective parts in synchrony.

Figure 5:
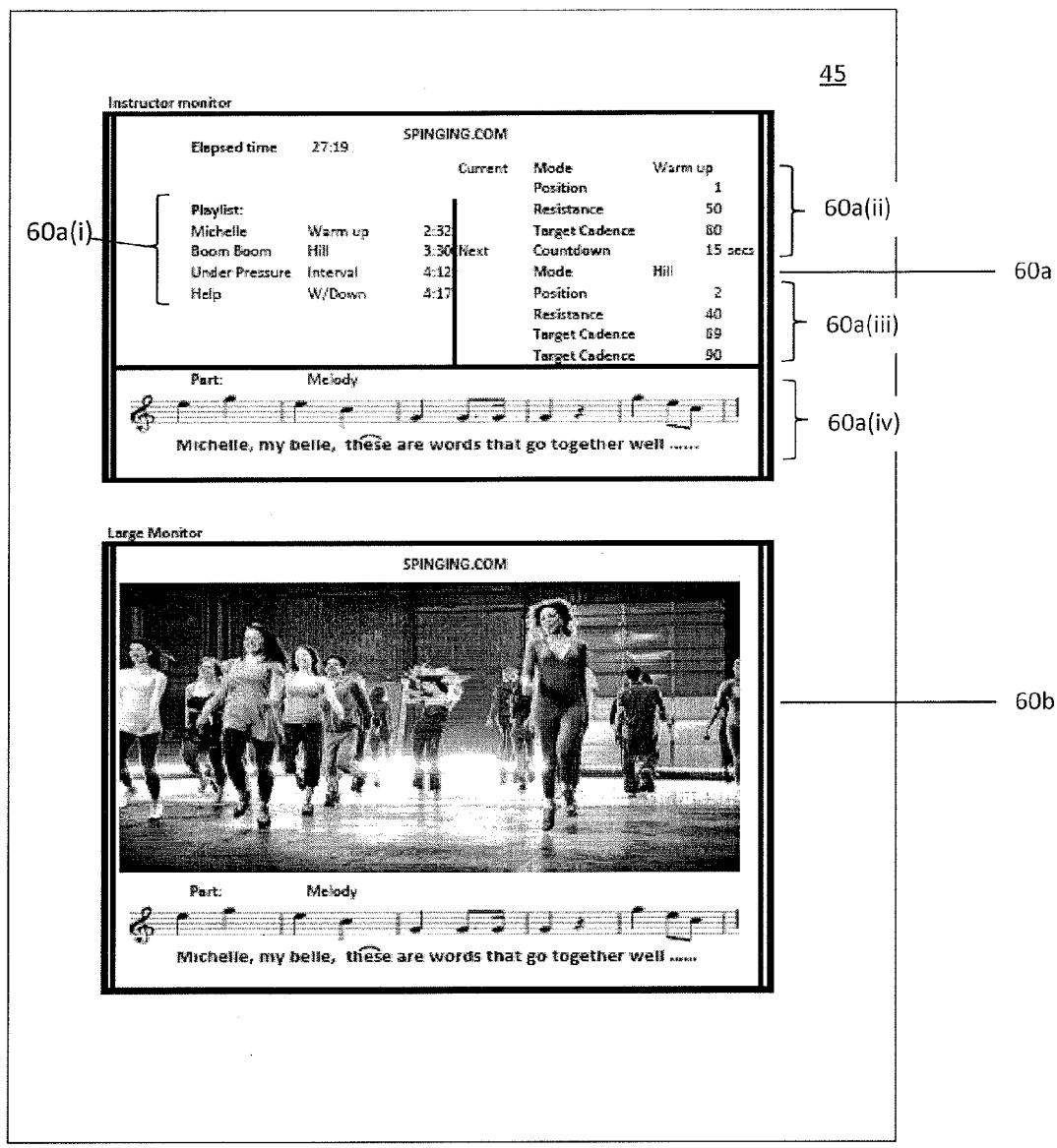
FIG. 5 is an exemplary screenshot of a screen of an "exersing" application displayed on the display of the computer system of FIG. 3.

FIG. 5, depicts an exemplary screenshot 60a of the instructor's display 45 during the "exersing" class. As shown, the instructor's monitor (for example, on the instructor's bike console or computing device), may display multiple elements comprising the playlist of songs, the segment of the exercise routine, and the songs' playtimes. For example, as shown on the left-hand side of screenshot 60a (section 60a(i)), the first song in the playlist is "Michelle" and it plays during the "Warm up" part of the exercise routine, and it lasts for 2 minutes and 32 seconds. The song "Boom Boom" plays during the "Hill" part of the exercise routine, and it plays for 3 minutes 30 seconds, and so on. The right-hand side of screenshot 60a (section 60a(ii)) displays information and targets related to the current part of the exercise routine, namely, the "Mode" (i.e. "Warm up"), the "Position", corresponding to the position on the bike that the exerciser is to assume; "Resistance" corresponding to the suggested resistance level that the exerciser should set his or her bike at; the "Target Cadence" corresponding to the suggested RPMs that the exerciser should maintain during the current mode; and "Countdown" corresponding to the time remaining in the current mode. Section 60a(iii) displays information and targets related to the next part of the exercise routine. Section 60a(iv) of screenshot 60a, displays a musical score related to the music that is currently playing, as shown, the melody part of the song "Michelle", as well as the lyrics to the song. Conveniently, the instructor, reading the music, may be able to lead the class participants in a sing along. In addition, the instructor may read off the resistance and target cadence levels displayed on his or her screen and call them out to the class participants.

FIG. 5 is an exemplary screenshot 60b of what may be displayed on a common "exersing" class monitor/screen for all class participants to view. As can be seen, this may include a motivational video of people exercising and the music for the currently playing song, "Michelle".

Furthermore, as previously discussed, "exersing" application 48 may allow the user (e.g. the class instructor or class participant) to choose which elements he or she wishes to see presented on the common classroom screen/monitor (display 45) or bike console display (display 55) which, alternatively, may be a user's smart phone or tablet, respectively. More specifically, and as further explained below, each "exersing" exercise package may comprise multiple elements such as audio, video, music, lyrics, text, graphics and animation, which elements may be selectively turned on or off at runtime by the user, via, for example, the GUI illustrated in FIG. 13. Thus, for example, if the user wishes only to experience the instrumental part of a song and no vocals (i.e. lyrics), he or she may select (i.e. turn on) the instrumental option and deselect (i.e. turn off) the vocal option. Similarly, if the user wishes to have the sheet music accompanying the song scrolled across his or her screen, he may select this option.

Figure 13:
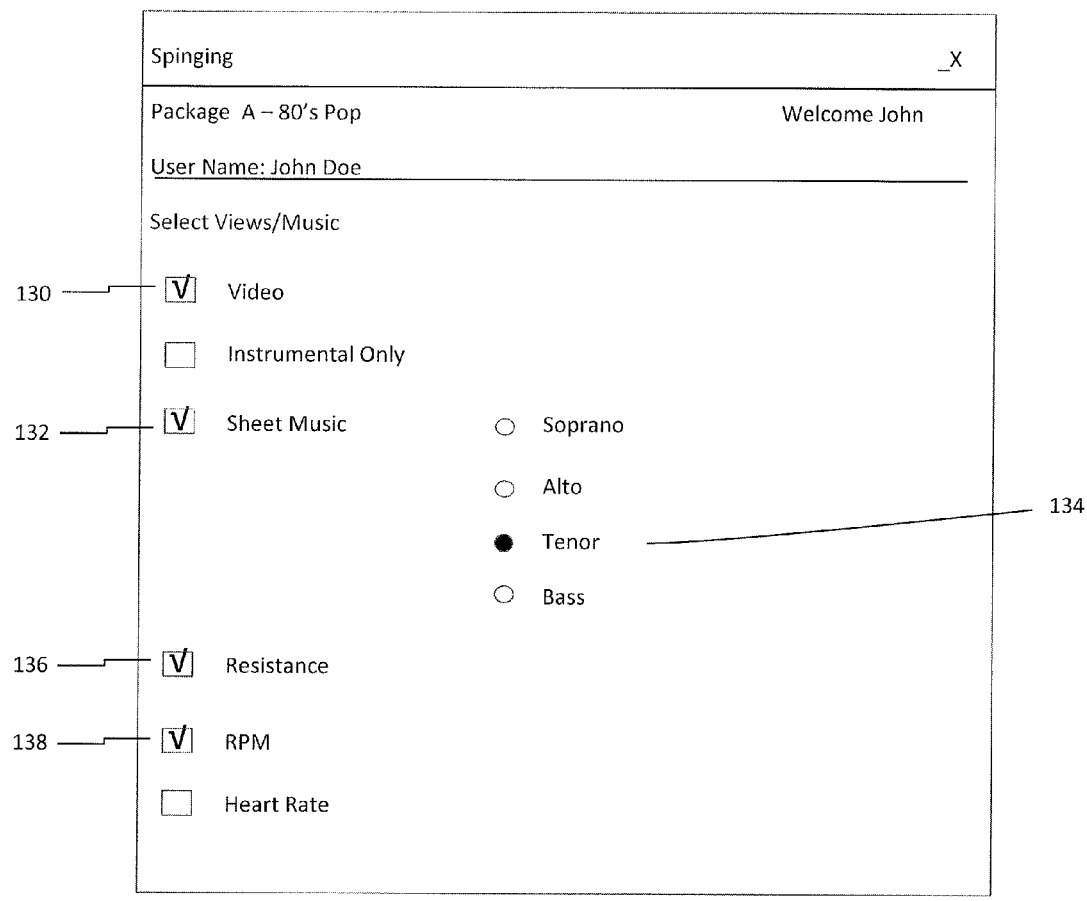
FIG. 13 is a screenshot of an exemplary graphical user interface presented on the display of the computer system of FIG. 4.

Returning to the above example, each of Abigail and John may, at the start of the class, select, via a GUI presented by "exersing" application 58 running on his or her bike (FIG. 13), which elements he or she wishes to experience. FIG. 13 is a screenshot of an exemplary screen that may be presented to John on his device e.g. stationery bike console display 55. As may be seen, John has indicated, by selecting selection boxes 130, 132, 136, 138, that he wishes to have video, sheet music, resistance level and rpms displayed on his bike console display 55. In particular, he has indicated by selecting radio button 134 that the sheet music should correspond to the tenor part of each song.

FIG. 6 illustrates what may be displayed on an individual class participant's display 55 of his or her computing device or bike monitor during an "exersing" e.g. "spinging" class. More specifically, screenshot 70a shows one possible view which includes the time elapsed in the exercise routine (section 70a(i)); resistance level, target cadence, actual cadence, heart rate and calories/Kwh (section 70a(ii)); and music related to the currently playing song (section 70a(iii)). Notably, the information displayed in section 70a(ii) may be information pertaining specifically to that individual class participant and may be obtained from that individual's device e.g. bike console and/or external devices that are synced and in communication with that individual's bike (e.g. heart rate monitor strapped to that individual's chest which transmits heart rate data to the bike).

Screenshot 70b illustrates an alternate view of a class participant's display 55. In particular, section 70b(i) displays a diagram of the exercise room and indicates the name of each "exersing" class participant riding e.g. each stationary bike rider. Upon logging in to his or her exersing computing device, each class participant may select to share their name and provide it to the facility's computer system 14, which in turn, may collect and consolidate and send back the information to each individual's computing device. Notably, section 70b(ii) of screenshot 70b displays music for the bass part of the song "Michelle", because that particular individual may sing in the bass range, in contrast to, for example, the music displayed in section 70a(iii) of screenshot 70a, which is for the soprano part of the song "Michelle", because that individual may sing in the soprano range. Advantageously, the music and lyrics may scroll across each individual's device e.g. bike console display at the same rate so that all of the class participants may sing their respective parts in synchrony.

Conveniently, and as discussed previously, instead of attending a group exercise class, an individual subscriber may choose to instead experience a particular "exersing" package to which he or she has licensed on his or her own time in his or her location of choice (e.g. at home) ("single user mode"). Flow diagram 4000 (FIG. 12) illustrates operation of an individual user's computing device. In this example, "exersing" application 58 on the user's computing device 12 may receive the user's credentials (S4010, FIG. 12) as well as an indication of the exercise package routine to be initiated (S4012). "Exersing" application 58 may then access the package (either stored on computing device 12), or over a network if stored remotely. "Exersing" application 58 may include a GUI similar to the GUI presented by "exersing" application 48 hosted on facility computer system 14 (see FIG. 13), which allows the user to pre-select, or select at runtime, which elements of the "exersing" exercise routine he or she wishes to see or hear. "Exersing" application 58 may then display a version of the exercise routine that may be customized to that particular user (S4014) based upon the options selected by the user.

In addition, in accordance with an alternate embodiment of the present application, multiple individuals running "exersing" application 58 in single user mode may form an ad hoc group and may thereby experience a group exercise session without the needing a human instructor. More specifically, "exersing" application 58 running on one of the class participant's devices may be designated as the "master" and the others as "slaves". The "master" may send information, including timing information, to the "slaves", and in this fashion, keep all the class participants in synchrony.

Implementation of "exersing" application 38, 48 and 58, and in particular, implementation of combining and superimposing streams of static text and graphics, subtitles and scrolling/dynamic text/graphics on a video or on a still background are known to those of ordinary skill in the art. In particular, implementation of "exersing" application 38, 48 and 58 may include known and conventional technology and techniques, e.g. karaoke and video editing/display technology. For example, data structures for representing the components of a karaoke song (e.g. .kar file format) may be used. Conversely, known techniques for reading and executing a .kar file may be employed.

Operation of system 20 with respect to the administration and distribution of pre-packaged exercise routines (i.e. "exersing" exercise packages) has been described above. However, significantly, system 20 may further allow users to create/compile new "exersing" routines (i.e. new exercise packages), so that new content may be supplied to subscribers of the "exersing" service. In particular, "exersing" application 38 hosted on the central facility computer system 10 (server-side application) may allow a user—for example, an employee or administrator of the "exersing" service provider—to create new exercise packages.

In particular, "exersing" application 38 hosted on central facility computer system 10 (server-side application) may allow a content producer, for example, an employee of the "exersing" service provider to create new "exersing" exercise packages, including a single song, or a collection of songs (analogous to an album) synchronized to an exersing routine. Optionally, a subscriber to the "exersing" service (e.g. an individual subscriber or a facility), may also create exercise packages. The "exersing" service provider may purchase or license content, specifically, songs, music videos, karaoke tracks, etc. to be included as part of one or more exercise packages. Furthermore, the "exersing" service provider may purchase or create additional elements/content related to each song such as sheet music, lyrics associated with the songs, resistance levels, elapsed time, etc. Techniques for separating a song into streams of data including melody, lyrics, harmony, beat and tempo are known.

Such content may be catalogued and stored in a content database (not shown) hosted on central facility computer system 10 for retrieval. The songs may be indexed in a conventional manner by various attributes, including type of music (e.g. instrumental or song); genre; era; beat count (e.g. 180 beats/min); vocal parts; language; artist/composer; publishing company; exercise type (warm-up, interval, hill climb, cool down); and others. Conveniently, the additional elements/content associated with each song may be included in the "exersing" exercise package. It is these additional elements/content that may be selected or deselected for presentation by individual exercisers during an exercise class, as explained previously.

Figure 14:
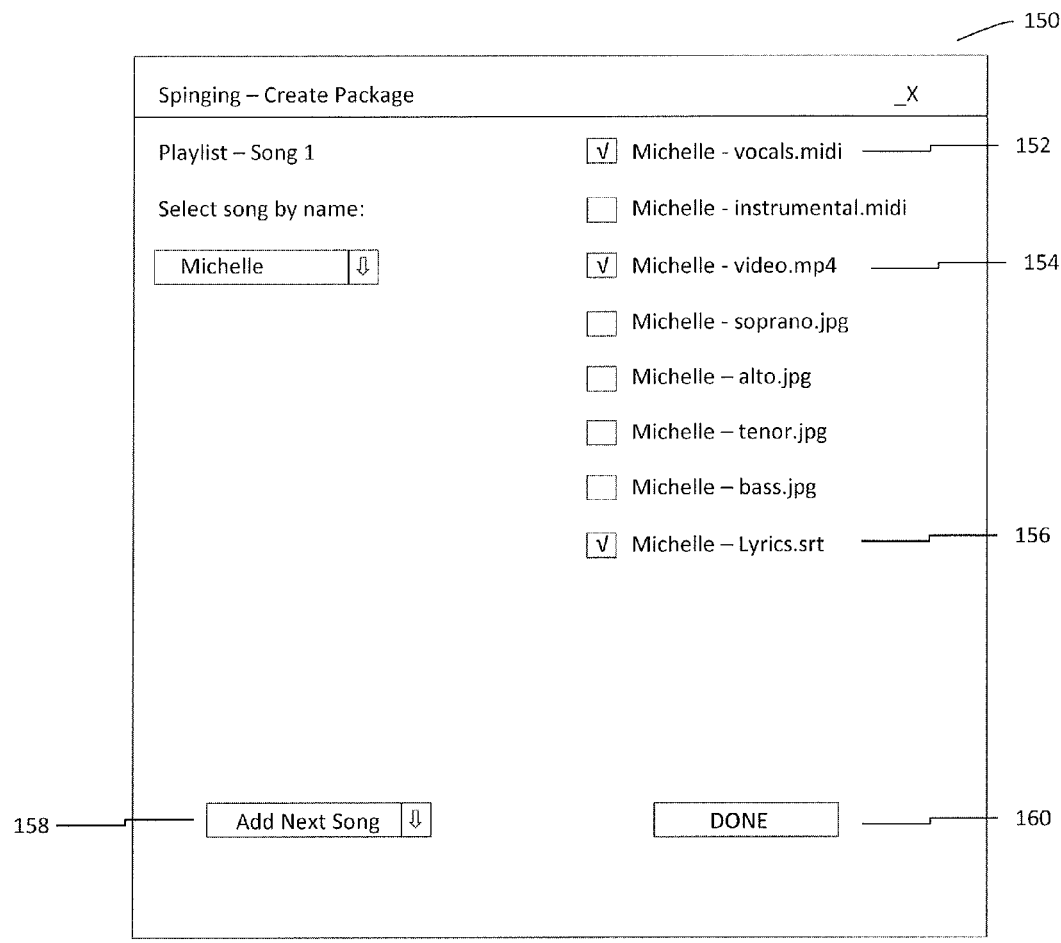
FIG. 14 is a screenshot of an exemplary graphical user interface presented on the display of the computer system of FIG. 10A.

In operation, a content producer may create new exersing packages by creating a playlist of songs. The content producer may design an exersing package according to various factors such as exercise type; duration of exercise; intensity of the exercise; degree of difficulty; etc. With this in mind, the content producer may first search for songs by one or more of the catalogued attributes indicated above (e.g. a low beat count for a song to be played during the warm-up segment of the exercise routine), via a conventional GUI (not shown). For each song, the "exersing" application 38 may present the available additional content via a GUI. FIG. 14 is a screenshot of an exemplary GUI 150 which presents the available additional elements/content related to the song "Michelle". In particular, FIG. 14 indicates that the following additional elements/content related to the song "Michelle" are available: a vocal track (Michelle_vocals.midi); instrumental track (Michelle_instrumental.midi); a video (Michelle_video.mp4); sheet music for the soprano, alto, tenor and bass parts (Michelle_soprano.jpg; Michelle_ alto.jpg; Michelle_tenor.jpg; Michelle_bass.jpg, respectively); and the lyrics (as a subtitle file Michelle_lyrics.srt).

Via exemplary GUI 150, the content producer may select the additional elements/content to be associated with the song "Michelle" in the "exersing" package. As shown, the content producer has chosen to include the vocal track, the video and the lyrics as indicated by selection boxes 152, 154, and 156. The content producer may add another song to the playlist by clicking button 158 or indicate he or she is done creating the playlist by clicking button 160. Once done, "exersing" application 38 may compile the playlist, which as should now be apparent, may include songs and all additional elements/content selected by the content producer and package it into a composite file. This file may be named, e.g. "Exersing package A", and stored by central facility computer system 10 for download/access by subscribed users.

As may be appreciated by those of ordinary skill in the art, system 20 may provide any number of additional features. For example, subscribers may choose to provide personal information (e.g. medical information) such as calories burned, maximum heart rate, medical conditions, age, etc. to central facility 22. Such information may be stored in subscriber database 23, for example, as additional attributes in exemplary SUBSCRIBER table 70 (FIG. 7A).

Moreover, central facility 22 may maintain a social networking site or members area website where subscribers may leave their comments, suggestions and communicate with each other. In particular, participants may, with other members' permission, be able to view who has registered for a class and/or who is attending a class in progress. A member may choose to allow other participants to view varying amount of information—e.g. friends, "exersing" classmates, information about themselves e.g. music interests, favourite music genre and artists, other interests and also invite communication e.g. "meet for coffee", "attend concert", "make music" from other members to varying degrees e.g. friends, "exersing" classmates.

Possibly, a camera may be placed at the exercise facility 22 and images of the members 24 exercising at a particular location may be captured, provided to computer system 10, for distribution to other individual members 24, remote from the exercise facility 22 by way of network 100. The camera may encode and stream moving video, thereby allowing remote members to view activities at the exercise facility 22.

As will be apparent, the purpose of the described methods and system is to facilitate singing while exercising. This may conveniently be made possible by providing words and music for singing coupled to synchronized exercise instructions. The basic level of singing while exercising involves an individual participant (or all participants in a group exercise class) singing along to the music piece. Advanced levels provide the words and music for multiple parts e.g. soprano, alto, tenor and bass to facilitate singing harmonies etc.

Health and other benefits of so singing while exercising are numerous and include: raising a participant's heart rate several beats above exercising only levels; increased enjoyment and, consequently, motivation to participate.

Singing while exercising with a group is fun and social. Making music with others creates a bond and increases the opportunity for and encourages social interaction.

This, in turn, may increase the market and appeal for combined exercising and singing, attracting a broader range of exercise participants. In addition the flexibility of "exersing" allows it to be marketed to a wide range of age groups and market segments to attract those who traditionally do not exercise. An area of significant public concerns currently is childhood obesity. Creating "exercising" packages for schools, youth clubs etc. may provide benefits. Retired and elderly people are also potential users.

Of course, the above-described embodiments are intended to be illustrative only and in no way limiting. The described embodiments of carrying out the invention are susceptible to many modifications of form, arrangement of parts, details and order of operation. The invention, rather, is intended to encompass all such modification within its scope, as defined by the claims.

What is claimed:

1. A computer-implemented method for facilitating a karaoke performance while exercising during an individual exercise session or group exercise class, comprising:
   receiving an indication of a song to be performed during said session or exercise class;
   retrieving at least one computer-readable karaoke file corresponding to said song, wherein said at least one computer-readable karaoke file comprises common data elements, at least two independent karaoke data streams and exercise-related data elements;
   receiving from a first class participant a selection of a first karaoke data stream of said at least two independent karaoke data streams;
   receiving from a second class participant a selection of a second karaoke data stream of said at least two independent karaoke data streams;
   directing presentation of said common data elements and said exercise-related data elements on a display common to said first and said second class participants;
   directing presentation of said first karaoke data stream on a display unique to said first class participant; and
   directing presentation of said second karaoke data stream on a display unique to said second class participant,
   wherein the presentation of said common data elements, said exercise-related data elements, said first karaoke data stream and said second karaoke data stream are synchronized.

2. The method of claim 1 wherein said first karaoke data stream comprises sheet music for a first vocal part of said song, said second karaoke data stream comprises sheet music for a second vocal part of said song, and further wherein said directing the presentation of said first karaoke data stream comprises presenting said sheet music for said first vocal part on a display viewed by said first class participant and said directing the presentation of said second karaoke data stream comprises presenting said sheet music for said second vocal part on a display viewed by said second class participant.

3. The method of claim 1 further comprising:
   presenting exercise-related data associated with said first class participant contemporaneously with said first karaoke data stream on said display unique to said first class participant; and
   presenting exercise-related data associated with said second class participant contemporaneously with said second karaoke data stream on said display unique to said second class participant.

4. The method of claim 1 wherein said common data elements comprises a video.

5. The method of claim 1 wherein said common data elements comprises lyrics to said song.

6. The method of claim 1 wherein said exercise-related data elements comprise an indication of at least one of: time elapsed in said exercise class, time to end of the song, segment of said exercise class, a target exercise intensity, and an exercise position.

7. The method of claim 1, further comprising: exchanging synchronization data between said first and second class participant to allow synchronized presentation of said common data elements, said exercise-related data elements, said first karaoke data stream and said second karaoke data stream.

8. A system for providing and managing access to karaoke files for use during individual and group exercise routines, comprising:
- a first computing device hosting a memory storing a plurality of computer-readable karaoke files adapted for use during individual and group exercise classes, wherein each of said karaoke files comprise common data elements, at least two independent data streams and exercise-related data elements;
- a plurality of exercise class participation devices, each in communication with said first computing device over a communications network, each of said exercise class participation devices further comprising at least one processor executing an application directing selective presentation of data on an individual display of that exercise class participation device;
- a second computing device in communication with said plurality of exercise class participation devices and said first computing device, said second computing device hosting an application directing presentation of said common data elements and said exercise-related data elements on a common display common to all class participants and presentation of certain selected independent data streams on individual displays of certain ones of said plurality of exercise class participation devices.

9. The system of claim 8 wherein said common data elements comprises a video.

10. The system of claim 8 wherein said common data elements comprises lyrics to said song.

11. The system of claim 8 wherein said exercise-related data elements comprise an indication of at least one of: time elapsed in said exercise class, time to end of the song, segment of said exercise class, a target exercise intensity, and an exercise position.

12. The system of claim 8, wherein at least some of said individual displays are co-located.

13. The system of claim 12, wherein at least one of said individual displays is remote from remaining individual displays.

14. The system of claim 8, further comprising a camera for capturing images of at least some participants in a group of participants using said exercise class participation devices.

15. The system of claim 14, wherein said camera transmits said images to remote participants.

16. The system of claim 14, wherein each of said plurality of exercise class participation devices comprises a stationary bike.

* * * * *